United States Patent [19]

Tsuchiya et al.

[11] 4,307,721
[45] Dec. 29, 1981

[54] NON-WOVEN FABRIC FOR SANITARY NAPKIN

[75] Inventors: Yoshimi Tsuchiya, Utsunomiya; Hiroshi Mizutani, Yachiyo, both of Japan

[73] Assignee: Kao Soap Co., Ltd., Tokyo, Japan

[21] Appl. No.: 171,055

[22] Filed: Jul. 22, 1980

[30] Foreign Application Priority Data

Aug. 7, 1979 [JP] Japan .................. 54-100418

[51] Int. Cl.³ .................................. A61F 13/16
[52] U.S. Cl. ........................... 128/290 W; 428/212; 428/298
[58] Field of Search ............ 128/284, 290 R, 296, 128/156, 290 W, 285; 428/212–213, 219, 298, 224

[56] References Cited

U.S. PATENT DOCUMENTS

| | | | |
|---|---|---|---|
| 2,862,251 | 12/1958 | Kalwaites | 128/290 W |
| 3,420,235 | 1/1969 | Harmon | 128/290 R |
| 3,695,269 | 10/1972 | Malaney | 128/284 |
| 3,804,092 | 4/1974 | Tunc | 128/284 |
| 4,129,132 | 12/1978 | Butterworth et al. | 128/287 |
| 4,145,464 | 3/1979 | McConnell et al. | 128/284 |

*Primary Examiner*—C. Fred Rosenbaum
*Attorney, Agent, or Firm*—Blanchard, Flynn, Thiel, Boutell & Tanis

[57] ABSTRACT

There is disclosed a non-woven fabric suitable as the envelope for a sanitary napkin which has an integrated three-layer structure including a first layer forming the surface falling in contact with the skin, a third layer forming the back face and a second layer interposed between said two layers, said envelope being characterized in that (a) the first layer is composed of rayon fibers having 1.5 to 3 deniers and thermoplastic fibers, the weight ratio of the rayon fibers to the thermoplastic fibers is in the range of from 40/60 to 70/30 and the rayon fibers and thermoplastic fibers are densely compacted (b) the second layer is composed of rayon fibers having a fineness of 3 to 7 deniers and thermoplastic fibers, the weight ratio of the rayon fibers to the thermoplastic fibers is in the range of from 60/40 to 90/10 and the rayon fibers and thermoplastic fibers are loosely compacted, (c) the third layer is composed of rayon fibers having a fineness of 1.5 to 3 deniers and thermoplastic fibers and the weight ratio of the rayon fibers to the thermoplastic fibers is in the range of from 40/60 to 90/10, and (d) the entire basis weight of the three layers is 15 to 30 g/m².

2 Claims, 2 Drawing Figures

NON-WOVEN FABRIC FOR SANITARY NAPKIN

The present invention relates to a non-woven fabric for a sanitary napkin. More particularly, the present invention relates to a non-woven fabric for a sanitary napkin, which has a three-layer structure composed of mixed fibers of rayon fibers and thermoplastic fibers, in which the density, the fiber fineness and the mixing ratio of the rayon fibers and thermoplastic fibers are different among the respective layers.

Sanitary napkins available on the market have a structure in which the back face and side face of an absorbing material such as absorbent paper or pulp are covered with an impervious layer and the assembly is entirely covered with a non-woven fabric. The sanitary napkin of this type has a shape convenient for handling but it is still insufficient in various points as regards the functions thereof. As the problem to be solved in the non-woven fabric as the envelope, there can be mentioned a phenomenon called "wet back". That is, when an external pressure is applied, the once absorbed menstruation blood is returned to the skin through the surface of the non-woven fabric. Furthermore, in some fibers, there is observed a phenomenon of falling of fibers from the non-woven fabric, and it often happens that the menstruation blood is not absorbed but it flows on the surface of the non-woven fabric. Moreover, in order to prevent leakage in the longitudinal direction, both the ends of the non-woven fabric should be heat-sealed.

Various researches have heretofore been made so as to eliminate these defects. For example, the specification of U.S. Pat. No. 3,420,235 discloses an envelope of non-woven fabric comprising 25 to 75% of rayon and 75 to 25% of polypropylene, and it is taught that this envelope is excellent in the touch to the skin and the heat-sealability. Furthermore, Japanese Utility Model Publication No. 35353/72 discloses that a rayon paper or thermoplastic fiber non-woven fabric having a thin layer of rayon staple cotton bonded to the inner face thereof is used, the spot absorption characteristic and the cushioning property at the time of application are improved and falling of fibers is prevented. Indeed, the functions of sanitary napkins are improved according to these known techniques, but the required functions cannot be satisfactorily obtained. For example, the former envelope has a fatal defect of the lateral leakage of the menstruation blood flowing on the surface of the non-woven fabric. We have made researches with a view to overcoming these defects and obtaining an excellent non-woven fabric, and we have succeeded in obtaining a novel non-woven fabric for a sanitary napkin having excellent properties while eliminating the above-mentioned defects by adopting a specific three-layer structure for the envelope.

More specifically, in accordance with the present invention, there is provided a non-woven fabric suitable for the envelope for a sanitary napkin which has an integrated three-layer structure including a first layer forming the surface falling in contact with the skin, a third layer forming the back face and a second layer interposed between said two layers, said envelope being characterized in that (a) the first layer is composed of rayon fibers having a fineness of 1.5 to 3 deniers and thermoplastic fibers, the weight ratio of the rayon fibers to the thermoplastic fibers is in the range of from 40/60 to 70/30 and the rayon fibers and thermoplastic fibers are densely compacted in the paper-like form, (b) the second layer is composed of rayon fibers having a fineness of 3 to 7 deniers and thermoplastic fibers, the weight ratio of the rayon fibers to the thermoplastic fibers is in the range of from 60/40 to 90/10 and the rayon fibers and thermoplastic fibers are loosely compacted, (c) the third layer is composed of rayon fibers having a fineness of 1.5 to 3 deniers and thermoplastic fibers and the weight ratio of the rayon fibers to the thermoplastic fibers is in the range of from 40/60 to 90/10, and (d) the entire basis weight of the three layers is 15 to 30 g/m$^2$.

1: first layer, 2: second layer, 3: third layer,
4: non-woven fabric, 5: absorbent tissue,
6: fluffed pulp, 7: polyethylene-laminated waterproof paper The present invention will now be described with reference to the accompanying drawings.

Figure 1:
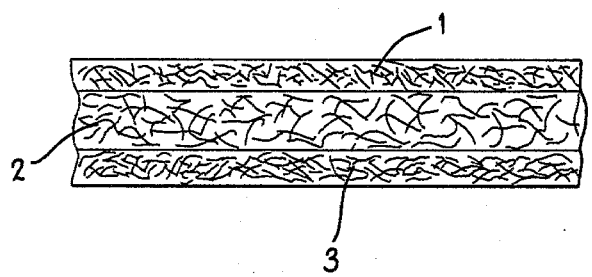
FIG. 1 is an enlarged sectional view illustrating one embodiment of the non-woven-fabric of the present invention.

Referring to FIG. 1 showing the structure of the non-woven fabric for a sanitary napkin according to the present invention, it has an integrated three-layer structure including a first layer 1 forming the surface falling in contact with the skin, a third layer 3 forming the back face and a second layer 2 interposed between said two layers. Each of these layers is composed of mixed fibers of rayon fibers and thermoplastic fibers, but the fineness of rayon fibers, the mixing ratio of both the fibers and the density are different among the respective layers. More specifically, in the first layer 1, the mixing weight ratio of the rayon fibers to the thermoplastic fibers is in the range of from 40/60 to 70/30 and the fineness of the rayon fibers is 1.5 to 3 deniers. The mixed fibers are densely compacted in the paper-like form, but the density need not be uniform but is ordinarily reduced toward the second layer 2. In the second layer 2, the mixing weight ratio of the rayon fibers to the thermoplastic fibers is in the range of from 60/40 to 90/10, and the fineness of the rayon fibers is 3 to 7 deniers. In the mixed fibers of the second layer 2, the fineness of the rayon fibers is larger than in the first layer 1 and the ratio of the rayon fibers is higher than in the first layer 1. Since the conduction of heat is small at the forming step, the density is low and the fibers are loosely compacted. In the third layer, the mixing weight ratio of the rayon fibers to the thermoplastic fibers is in the range of from 40/60 to 90/10 and the fineness of the rayon fibers is 1.5 to 3 deniers. The base weight of the entire structure is 15 to 30 g/m$^2$. The proportions of the three layers are not particularly critical, but from the viewpoint of the bulkiness of the second layer, it is preferred that the proportion of the second layer be larger. It also is preferred that the proportions of the three layers be adjusted so that the ratio of fine rayon fibers having a fineness of 1.5 to 3 deniers to thick rayon fibers having a fineness of 3 to 7 deniers is in the range of 10/90 to 70/30 in the entire structure. Furthermore, it is preferred that the mixing weight ratio of the rayon fibers to the thermoplastic fiber in the entire three-layer structure be adjusted in the range of from 50/50 to 80/20.

Various advantages described below are attained by the non-woven fabric of the present invention having the above-mentioned structure.

Rayon is excellent in the touch to the skin and the moisture-absorbing property but since it has no self-adhesiveness, a binder must be used for forming a non-woven fabric from rayon. In a non-woven fabric or rayon formed by using such binder, however, characteristic properties of rayon are degraded, and the non-woven fabric is hard and inferior in the touch. Accordingly, an envelope suitable for a sanitary napkin cannot be obtained from such non-woven fabric of rayon. Thermoplastic fibers show a self-adhesiveness under heating, and the degree of adhesion can be controlled by changing the heating temperature and time. However, thermoplastic fibers have no moisture-absorbing property, and in a non-woven fabric envelope of thermoplastic fibers, the menstruation blood flows on the surface of the envelope, causing lateral leakage.

In the non-woven fabric of the present invention, by mixing both the rayon fibers and thermoplastic fibers appropriately, characteristic properties of both the fibrs can be effectively utilized, and excellent properties can be obtained by changing the fineness and the mixing ratio.

Since the rayon fibers used for the first layer 1 are fine (1.5 to 3 deniers), the first layer 1 has a good touch to the skin, and since the mixing ratio of the thermoplastic fibers is relatively high i.e., 30 to 60% by weight and the first layer 1 is densely compacted in the paper-like form, falling or raising of fibers is not caused and repelling of the menstruation blood or expansion of the menstruation blood on the surface can be prevented. Furthermore, since rayon fibers absorb the menstruation blood but thermoplastic fibers do not absorb the menstruation blood, the menstruation blood is immediately spot-absorbed in the absorbing layer.

In the second layer 2, since the mixing ratio of thermoplastic fibers is relatively low i.e., 10 to 40% by weight and the conduction of heat is small at the forming step, the fibers are loosely compacted as in cotton, and since the fineness of rayon Fibers used is large (3 to 7 deniers), the second layer has a good bulkiness and a strong nerve, and therefore, the cushioning property is very good. Furthermore, this good bulkiness exerts an effect of preventing the return of the menstruation blood.

In the third layer 3, since the fineness of rayon fibers used is small (1.5 to 3 deniers), the entire touch is improved. If the mixing ratio of the rayon fibers is 40 to 70% by weight, the strength of the entire structure is improved and the effect of reducing occurrence of mechanical troubles can be attained. If the mixing ratio of the rayon fibers in 70 to 90%, a good cushioning property is obtained. A preferred mixing ratio of the rayon fibers can optionally be chosen according to the desired touch or mechanical properties.

If the ratio of the rayon fibers to the thermoplastic fibers is the entire structure is adjusted in the range of from 50/50 to 80/20, a good touch is obtained and a sufficient strength is maintained.

Since the base weight of the entire structure is adjusted to 15 to 30 g/m$^2$, a necessary strength can be obtained while maintaining a good softness.

The non-woven fabric having the above-mentioned three-layer structure according to the present invention can easily be obtained by performing the carding operation with respect to each of the three layers, piling the three layers and passing the assembly between heating rollers. The densities of the three layers can optionally be changed by appropriately changing the heating temperature or the roll speed.

Any of thermoplastic fibers satisfying the above-mentioned requirements can be used in the present invention. For example, fibers of polyolefins such as polyethylene and polypropylene, polyesters, polyamides and acrylonitrile polymers are preferred, and polyolefin fibers are especially preferred because the manufacturing cost is low and they have good properties. The fineness of the thermoplastic fibers is not particularly critical and attainment of the above-mentioned effects is not influenced by the fineness of the thermoplastic fibers. However, it is ordinarily preferred that the fineness of the thermoplastic fibers used be 1.5 to 5 deniers.

The effects attained according to the present invention are summarized below.

(1) The liquid-abosorbing property on the surface of the non-woven fabric is good (good spot absorbing property).
(2) Raising or falling of fibers is not caused.
(3) Return of the liquid is prevented.
(4) Good bulkiness and cushioning property can be obtained.

From the Examples given hereinafter, it will readily be understood that the non-woven fabric according to the present invention has the above-mentioned excellent effects.

In carrying out the present invention, a thin layer of rayon cotton or the like may be bonded to the inner face of the non-woven fabric according to the present invention, whereby the cushioning property can be further improved.

EXAMPLE 1

Non-woven fabrics differing in the mixing ratio of constituent fibers were tested with respect to the softness and falling of fibers (the surface portion). The softness was evaluated based on the touch and falling of fibers was evaluated based on the number of fibers separated when the surface of the non-woven fabric was rubbed. The obtained results are shown in Table 1, where ◯ indicates a good condition, Δ indicates a relatively bad condition, and X indicates a bad condition.

TABLE 1

| Run No. | Layer Number | Mixing Ratio (% by Weight) of Rayon Fibers Denier Number | | | | | Thermoplastic Fibers Kind* | Mixing Ratio (% by weight) | Base Weight** (g/m$^2$) | Softness | Falling of Fibers |
| --- | --- | --- | --- | --- | --- | --- | --- | --- | --- | --- | --- |
| | | 1.5 | 2 | 3 | 5 | 7 | | | | | |
| 1 (product of present invention) | 1 | 70 | | | | | ES | 30 | 18 | ◯ | ◯ |
| | 2 | | | | 80 | | ES | 20 | | | |
| | 3 | 70 | | | | | ES | 30 | | | |
| 2 (product of present | 1 | | 60 | | | | ES | 40 | 19 | ◯ | ◯ |
| | 2 | | | | | 80 | ES | 20 | | | |
| | 3 | | 80 | | | | ES | 20 | | | |

TABLE 1-continued

| Run No. | | Layer Number | Mixing Ratio (% by Weight) of Rayon Fibers Denier Number | | | | | Thermoplastic Fibers Kind* | Mixing Ratio (% by weight) | Base Weight** (g/m²) | Softness | Falling of Fibers |
|---|---|---|---|---|---|---|---|---|---|---|---|---|
| | | | 1.5 | 2 | 3 | 5 | 7 | | | | | |
| 3 | invention) (comparative product) | 1 2 3 | | 80 70 | | 60 | | ES ES ES | 20 40 30 | 20 | ○ | X |
| 4 | (comparative product) | — | | 60 | | | | ES | 40 | 23 | △ | ○ |
| 5 | (comparative product) | — | 80 | | | | | ES | 20 | 20 | ○ | X |
| 6 | (comparative product) | — | | | | 60 | | ES | 40 | 19 | X | ○ |
| 7 | (comparative product) | 1 2 3 | | 70 70 | | 60 | | ES ES ES | 40 30 30 | 19 | △ | ○ |

Note
*ES indicates polyethylene-polypropylene composite fibers.
**The base weight is the weight per certain unit area.

EXAMPLE 2

Figure 2:
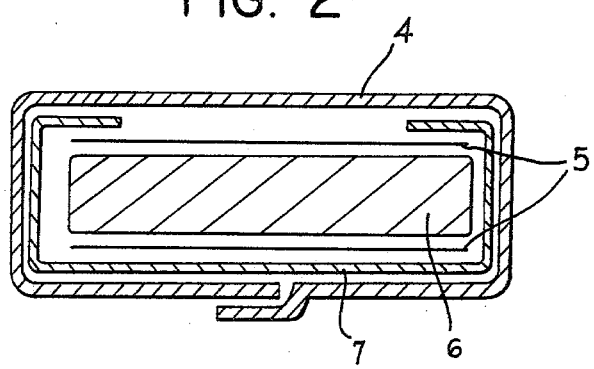
FIG. 2 is a sectional view showing the sanitary napkin used at the experiment of Example 2.

An inner layer comprising an absorbent tissue 5 having a weight of 0.6 g, a fluffed pulp 6 having a weight of 4.0 g and a polyethylene-laminated water-proof paper 7 having a weight of 0.6 g was wrapped with a non-woven fabric as shown in FIG. 2. The flow of the liquid on the surface, the amount of the return liquid and the dryness were tested with respect to the so obtained sanitary napkin.

The flow of the liquid on the surface was tested in the following manner.

The sanitary napkin was placed at an angle of 45° from the horizontal plane so that the skin-contacting face was located above. A blood-like liquid (1 ml) was dropped on the top end portion, and the distance along which the liquid flowed before it was absorbed was measured.

The amount of the return liquid was determined in the following manner.

After the liquid had been absorbed in the above-mentioned manner, a filter paper was placed on the top face and the assembly was pressed under 50 g/cm² for 3 minutes, and the amount of the liquid absorbed in the filter paper was measured.

The dryness was evaluated based on the feeling obtained when the surface of the non-woven fabric after absorption of the liquid was touched by the hand.

The obtained results are shown in Table 2.

TABLE 2

| Run No. | | Layer Number | Mixing Ratio (% by weight) of Rayon Fibers Denier Number | | | | | Thermoplastic Fibers Kind | Mixing Ratio (% by weight) | Base Weight (g/m²) | Surface Flow (mm) | Amount (g) of Return under Pressure | Dryness |
|---|---|---|---|---|---|---|---|---|---|---|---|---|---|
| | | | 1.5 | 2 | 3 | 5 | 7 | | | | | | |
| 8 | (product of present invention) | 1 2 3 | | | 55 70 | | 70 | ES ES ES | 45 30 30 | 18 | 30 | 3.0 | ○ |
| 9 | (product of present invention) | 1 2 3 | 65 | 70 | | 75 | | ES ES ES | 35 25 30 | 20 | 25 | 3.4 | ○ |
| 10 | (product of present invention) | 1 2 3 | 60 70 | | | 70 | | ES ES ES | 40 30 30 | 20 | 30 | 3.5 | ○ |
| 11 | (comparative product) | — | 65 | | | | | ES | 35 | 18 | 35 | 4.2 | X |
| 12 | (comparative product) | — | | | | 50 | | ES | 50 | 20 | 130 | 3.9 | △ |
| 13 | (comparative product) | 1 2 3 | | 30 70 | | | 70 | ES ES ES | 70 30 30 | 22 | 190 | 3.8 | △ |
| 14 | (product of present invention) | 1 2 3 | 60 | | 70 | | 70 | PP PP PP | 40 30 30 | 18 | 35 | 3.2 | ○ |
| 15 | (product of present invention) | 1 2 3 | | 55 70 | | | 80 | ES PET PET | 45 20 30 | 21 | 30 | 3.0 | ○ |
| 16 | (comparative product) | — | | 60 | | | | ES PET | 20 20 | 20 | 30 | 4.1 | △ |
| 17 | (comparative product) | — | | | | | | ES PET | 40 60 | 18 | 130 | 3.5 | ○ |
| 18 | (comparative product) | — | | | | | | ES | 100 | 19 | 150 | 4.2 | △ |

EXAMPLE 3

Comparative tests were carried out on a sanitary napkin wrapped with the non-woven fabric according to the present invention and a commercially available sanitary napkin. The inner layer used for the sanitary napkin according to the present invention had the same structure as that of the inner layer used in Example 2. The structure of the non-woven fabric was as follows.

|  | Rayon Fibers | | ES Fibers |
| --- | --- | --- | --- |
|  | 3 deniers | 5 deniers | 3 deniers |
| First layer | 55% by weight | | 45% by weight |
| Second layer | | 70% by weight | 30% by weight |
| Third layer | 70% by weight | | 30% by weight |

The obtained results are shown in Table 3.

TABLE 3

| Run No. | Non-Woven Fabric | Base Weight (g/m²) | Surface Flow (mm) | Amount (g) of Return Under Pressure | Dryness |
| --- | --- | --- | --- | --- | --- |
| 19 (product of present invention) | as described above | 19 | 25 | 2.9 | |
| 20 (commercial product A) | composed mainly of rayon (wet type), binder used | 20 | 150 | 4.4 | X |
| < (commercial product B) | composed mainly of rayon (dry type), binder used | 18 | 90 | 3.9 | X |
| 22 (commercial product C) | PP-rayon (dry type), binder used | 20 | 65 | 3.6 | Δ |

What is claimed is:

1. A non-woven fabric suitable as the envelope for a sanitary napkin which has an integrated three-layer structure including a first layer forming the surface falling in contact with the skin, a third layer forming the back face and a second layer interposed between said first and third layers, said envelope being characterized in that (a) the first layer is composed of rayon fibers having a fineness of 1.5 to 3 deniers and thermoplastic fibers, the weight ratio of the rayon fibers to the thermoplastic fibers is in the range of from 40/60 to 70/30 and the rayon fibers and thermoplastic fibers are densely compacted, (b) the second layer is composed of rayon fibers having a fineness of 3 to 7 deniers and thermoplastic fibers, the weight ratio of the rayon fibers to the thermoplastic fibers is in the range of from 60/40 to 90/10 and the rayon fibers and thermoplastic fibers are loosely compacted, (c) the third layer is composed of rayon fibers having a fineness of 1.5 to 3 deniers and thermoplastic fibers and the weight ratio of the rayon fibers to the thermoplastic fibers is in the range of from 40/60 to 90/10, and (d) the entire basis weight of the three layers is 15 to 30 g/m².

2. A non-woven fabric according to claim 1 wherein the thermoplastic fibers are polyolefin fibers.